United States Patent [19]

Koch et al.

[11] 4,020,093

[45] Apr. 26, 1977

[54] METHOD FOR SYNTHESIZING THIOCARBAMIC ACID ESTERS

[75] Inventors: Paolo Koch, S. Giuliano Milanese (Milan); Bartolomeo Anfossi, Milan, both of Italy

[73] Assignee: ANIC S.p.A., Palermo, Italy

[22] Filed: Apr. 20, 1976

[21] Appl. No.: 678,669

[30] Foreign Application Priority Data

Apr. 23, 1975 Italy .................................. 22617/75

[52] U.S. Cl. ....................... 260/455 A; 260/609 D; 260/609R
[51] Int. Cl.² ...................................... C07C 155/02
[58] Field of Search ........ 260/609 D, 609 C, 455 A

[56] References Cited

OTHER PUBLICATIONS

Org. Syn. vol. 18, pp. 673.

*Primary Examiner*—Lewis Gotts
*Assistant Examiner*—D. R. Phillips
*Attorney, Agent, or Firm*—Ralph M. Watson

[57] ABSTRACT

A method is disclosed for the preparation of thiocarbamic acid esters by reacting an aminic compound with carbon monoxide and an organic disulphide. Elemental selenium is used as the catalyst, possibly supplemented by a tertiary amine. The temperature and pressure ranges are comparatively wide.

10 Claims, No Drawings

METHOD FOR SYNTHESIZING THIOCARBAMIC ACID ESTERS

This invention relates to a method for the preparation of esters of thiocarbamic acids by carbonylation of aminic compounds and organic disulphides.

More particularly, the present invention relates to the preparation of esters of thiocarbamic acids starting from compounds corresponding to the formula:

$$X - (A)_n - NH_2$$

wherein A is an arylene radical, unsubstituted or substituted by halogens, hydrocarbon radicals, alkoxy groups, or it can be an alkylene radical, having from 1 to 15 carbon atoms, straight or branched, unsubstituted or substituted in which $n$ can be 0 or 1, whereas X can be hydrogen, $-NH_2$ or the group $H_2N-Z-$ in which the bivalent function, Z, derives from alkyl, aryl, cycloalkyl, alkylaryl, aralkyl radicals, which, in their turn, can be either unsubstituted or substituted.

These compounds are reacted with organic disulphides having the formula $R-S-S-R'$ in which R and R', equal to, or different from, one another, are substituted or unsubstituted hydrocarbonaceous radicals, and carbon monoxide, preferably in the presence of a catalyst, the latter being composed by elemental Se.

The importance of the esters of thiocarbamic acids is known, the latter finding applications both as pesticides and weedkillers, and also as intermediates for important organic syntheses, such as those of the isocyanates.

These esters of the thiocarbamic acids are prepared, at present, principally by the two following reactions: the first reaction consists in reaching an isocyanate with a mercaptan according to the following pattern:

The second reaction consists in reacting a primary organic amine with a chlorothiocarbonate, according to the following pattern:

wherein R and R' are hydrocarbon radicals.

These syntheses are affected by a considerable disadvantages in operation, since they start from products which are expensive and are difficult to be prepared.

As a matter of fact, in the case of isocyanate is used, this product is extremely costly, and, as is it required toxic products for its preparation also, its production is considerably hazardous.

Also in the second case, the use of chlorothiocarbonate is essentially expensive and dangerous.

It has now been found, and this is the subject matter of the present invention, that the synthesis of esters of thiocarbamic acids can be more appropriately carried out by reacting music compounds as defined above, with organic disulphides and carbon monoxide.

The reaction pattern in the case of the presence of one aminic group only, is as follows:

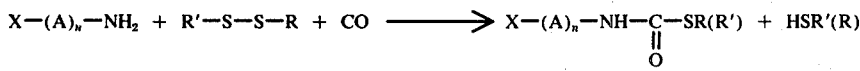

In the case of the presence of a second aminic group the above indicated reaction pattern is still practicable, or, as an alternative, the partial or total carbonylation of the second group will be obtained, consistently with the stoichiometry and the working conditions: it will be the task of those skilled in the art to select among those indicated below, without departing from the scope of the invention.

Such a synthesis thus permits that the esters of the thiocarbamic acid may be obtained without using costly or toxic reactants such as the isocyantes and the chlorothiocarbonates can be.

The preparation of such compounds, the subject matter of the present application, is effected by dissolving in an appropriate solvent (for example THF, acetonitrile, etc.) aminic compound and the disulphide in a stoichiometric amount. A catalyst system is then added, which is essentially composed by elemental selenium to which, in the case of aromatic amines, a tertiary amine (e.g. triethylamine) is added. Carbon monoxide is introduced in the solution under a pressure which may range between 1 and 200 atmospheres. The reaction temperature can be varied within a wide range as function of the starting aminic compound. It may be varied between $-20°$ C and $+150°$ C and, in the case of alkyleneamines it is preferred to work at the lower temperatures.

During progress of the reaction, mercaptan is formed, according to the stoichiometry, which can be oxidized to disulphide again in the same environment of the reaction.

The following illustrative by non-limiting examples show the method which is the subject-matter of the present invention, for obtaining the esters of the thiocarbamic acids.

EXAMPLE 1

In an autoclave having the volume of 150 mls there are introduced 0.93 grams of aniline, 0.94 grams of dimethyl disulphide, 0.030 grams of selenium, 0.360 grams of triethylamine and 20 mls of acetonitrile. The autoclave is filled with carbon monoxide under a pressure of 4 atmospheres and heated to 60° C with stirring.

During one hour, the 50% of the carbon monoxide which would be theoretically required by the stoichiometry of the reaction is consumed. A sufficiently long time is allowed to lapse to make sure that the remaining 50% of the carbon monoxide is consumed by the reaction. The autoclave is vented, and opened and the solution is evaporated off. The residue is dissolved in ethyl ether and the resultant solution is filtered. The undissolved portion (0.050 grams) is composed by selenium, which is thus recovered, and by N,N'-diphenylurea. The ethereal solution is evaporated off and the residue is crystallized from petroleum ether. There are obtained 1.6 grams of product which melts at 82° C and has a characteristic IR absorption in the 6-micron area. The elemental analysis has given the following results:

C = 58.1%; H = 5.8%; N = 8.4%; S = 20.58%; For $C_8H_9NOS$ there should be: C = 57.5%; H = 5.4%; N = 8.4%; S = 19.18%; Yield 95%.

EXAMPLE 2

Under conditions which were exactly similar to those of Example 1, there have been reacted 1.07 grams of p-toluidine, 0.94 grams of dimethyldisulphide, 0.030 grams of selenium and 0.360 grams of triethylamine in 20 mls acetonitrile. In 45 minutes the reaction consumes the 50% of carbon monoxide.

On completion of the reaction, by operating as in Example 1, there are isolated 0.050 grams of a product which is insoluble in ethyl ether and 1.7 grams of a product which melts at 107° C and exhibits a characteristic IR-absorption in the 6-micron area. Elemental analysis has given the following composition:

C = 59.6%; H = 6.4%; N = 7.4%; S = 18.30%; For $C_9H_{11}NOS$ there should be: C = 59.3%; H = 6.6%; N = 7.7%; S = 17.60%; Yield 94%.

EXAMPLE 3

Under very much the same conditions as in Example 1, there have been reacted 1.28 grams of p-chloroaniline, 0.94 grams of dimethyldisulphide, 0.030 grams of selenium and 0.360 grams of triethylamine in 20 mls of acetonitrile. During 4 hours the reaction consumes the 50% of the carbon monoxide. On completion of the reaction by operating as in Example 1, there are isolated 0.070 grams of a product which is insoluble in ethyl ether and 1.9 grams of a product which melts at 139° C and has a characteristic IR absorption in the 6-micron area. Elemental analysis has given the following composition:

C = 47.6%; H = 4.1%; N = 7.3%; S = 16.2%; Cl = 18.1%; For $C_8H_8Cl\,NOS$ there should be: C = 47.6%; H = 4.0%; N = 6.9%; S = 15.9%; Cl = 17.6%; Yield 95%.

EXAMPLE 4

Under conditions which are exactly similar to those of Example 1 there have been reacted 0.93 grams of aniline, 1.78 grams of diisobutyldisulphide, 0.030 grams of selenium and 0.360 grams of triethylamine in 20 mls of acetonitrile. During one hour the reaction has consumed the 50% of the carbon monoxide. On completion of the reaction, by operating as in Example 1, there are isolated 0.064 grams of a product which is insoluble in ethyl ether and 1.8 grams of a product which melts at 110° C and has a characteristic IR absorption in the 6-micron area. The elemental analysis has given the following results:

C = 64.3%; H = 7.7%; N = 7.1%; S = 15.7%; For $C_{11}H_{15}NOS$ there should be: C = 63.1%; H = 7.2%; N = 6.7%; S = 15.3%; Yield 86%.

EXAMPLE 5

Under very much the same conditions as in Example 1 there have been reacted 0.93 grams of aniline, 1.78 grams of nor.butyldisulphide, 0.030 grams of selenium and 0.360 grams of triethylamine in 20 mls of acetonitrile. After one hour the reaction has consumed the 50% of the carbon monoxide. On completion of the reaction by operating as in Example 1 there are isolated 0.075 grams of a product which is insoluble in ethyl ether and 1.90 grams of a product which melts at 74° C and exhibits a characteristic IR absorption in the 6-micron area. Elemental analysis has given the following results:

C = 63.2%; H = 7.6%; N = 7.0%; S = 15.5%; For $C_{11}H_{16}NOS$ there should be: C = 63.1%; H = 7.2%; N = 6.7%; S = 15.3%; Yield 94%.

EXAMPLE 6

Under conditions which are exactly the same as in Example 1, there have been reacted 1.07 grams of p-toludine, 1.78 grams of diisobutylsulphide, 0.030 grams of selenium and 0.360 grams of triethylamine in 20 mls of acetonitrile. During 30 minutes the reaction uses up 50% of the carbon monoxide. On completion of the reaction, by operating as in Example 1, there are isolated 0.140 grams of a product which is insoluble in ethyl ether and 2.0 grams of a product which melts at 70° C and displays a characteristic IR bands at 6 microns. Elemental analysis has given the following results:

C = 63.6%; N = 6.2%; S = 14.8%; H = 7.4%; For $C_{12}H_{17}NOS$ there should be: C = 64.6%; H = 7.6%; N = 6.3%; S = 14.4%; Yield 90%.

EXAMPLE 7

Under very much the same conditions as in Example 1, there have been reacted 1.07 grams of m-toluidine, 1.78 grams of diisobutyldisulphide, 0.030 grams of selenium and 0.360 grams of triethylamine in 20 mls of aceto nitrile. During 50 minutes the reaction consumes the 50% of the carbon monoxide. On completion of the reaction, by operating as in Example 1, there are isolated 0.097 grams of a product which is insoluble in ethyl ether and 2.1 grams of a product which melts at 59° C and exhibits a characteristic IR band in the 6-micron area. Elemental analysis has given the following results:

C = 64.8%; H = 8.2%; N = 6.5%; S = 13.7%; For $C_{12}H_{17}NOS$ there should be: C = 64.6%; H = 7.6%; N = 6.3%; S = 14.4%; Yield 94%.

EXAMPLE 8

Under very much the same conditions as in Example 1, there have been reacted 1.07 grams of o-toluidine, 1.78 grams of diisobutyldisulphide, 0.030 grams of selenium and 0.360 grams of triethylamine in 20 mls of of aceto nitrile. After 200 minutes the reaction has consumed the 50% of the carbon monoxide. On completion of the reaction by operating as in Example 1, there have been isolated 0.109 grams of a product which is insoluble in ethyl ether and 1.9 grams of a product which melts at 56° C and exhibits a characteristic IR absorption in the 6-micron area. Elemental analysis has given the following results:

C = 64.9%; H = 8.2%; N = 6.5%; S = 15.2%; For $C_{12}H_{17}NOS$ there should be: C = 64.6%; H = 7.6%; N = 6.3%; S = 14.4%; Yield 85%.

EXAMPLE 9

Under very much the same conditions as in Example 1, there have been reacted 1.28 grams of p-chloroaniline, 1.78 grams of diisobutyldisulphide, 0.030 grams of selenium and 0.360 grams of triethylamine in 20 mls of aceto nitrile. After 100 minutes the reaction has consumed the 50% of the carbon monoxide. On completion of the reaction by operating as in Example 1 there have been isolated 0.088 grams of a product which is insoluble in ethyl ether and 2.2 grams of a product which melts at 102° C and shows a characteristic IR absorption in the 6-micron area.

The elemental analysis has given the following results:

C = 55.5%; H = 6.1%; Cl = 14.5%; N = 6.0%; S = 13.0%; For $C_{11}H_{14}ClNOS$ there should be: C = 54.2%; H = 5.7%; Cl = 14.5%; N = 5.7%; S = 13.1%; Yield 90%.

EXAMPLE 10

Under very much the same conditions as in Example 1, there have been reacted 1.28 grams of m-chloroaniline, 1.78 grams of diisobutyldisulphide, 0.030 grams of selenium and 0.360 grams of triethylamine in 20 mls of aceto-nitrile. After 350 minutes the reaction has consumed the 50% of the carbon monoxide. On completion of the reaction and by operating as in Example 1, there are obtained 0.063 grams of a product which is insoluble in ethyl ether and 2.3 grams of a product which melts at 68° C and exhibits a characteristic IR absorption in the 6-micron area. The elemental analysis has given the following results:

C = 55.8%; H = 6.2%; Cl = 14.8%; N = 6.2%; S = 13.5%; For $C_{11}H_{14}ClNOS$ there should be: C = 54.2%; H = 5.7%; Cl = 14.5%; N = 5.7%; S = 13.1%; Yield 94%.

EXAMPLE 11

A 150-mls autoclave is charged with 2.1 grams of p-toluidine, 1.78 grams of diisobutyldisulphide, 0.030 grams of selenium, 0.360 grams of triethylamine and 20 mls of acetonitrile. The autoclave is filled with carbon monoxide at the pressure of 4 atmospheres and heated to 60° C with stirring. When carbon monoxide consumption is no longer recorded, the autoclave is discharged of its gas and carefully scavenged with an inert gas ($N_2$, Ar). It is then charged with air and it is waited until the mercaptan formed in the reaction is oxidized to disulphide again and generally this operation requires 15 minutes. The autoclave is subsequently discharged of its gas, carefully scavenged with an inert gas ($N_2$, Ar) and recharged with carbon monoxide at 4 atmospheres. These oxidizing and CO-reloading cycles are repeated four times. Lastly, the contents of the autoclave is treated as in Example 1. There have been thus obtained 0.49 grams of a product which is insoluble in ethyl ether and which is composed by a mixture of selenium and N,N'-di-p-tolyurea, and 3.5 grams of a product which melts at 70° C and exhibits the same composition as that of the product obtained in Example 6.

Yield 80%.

EXAMPLE 12

A 150-mls autoclave is charged with 2.2 grams of biphenyldisulphide, 0.94 grams of aniline, 0.030 grams of selenium, 0.360 grams of triethylamine and 20 mls of tetrahydrofuran. The autoclave is charged with carbon monoxide at a pressure of 4 atmospheres and heated to 60° C with stirring. After two hours the reaction has consumed the 50% of the carbon monoxide which is theoretically required by the reaction stoichiometry. A period of time is allowed to lapse which is sufficient to that the remaining 50% of carbon monoxide is consumed. The autoclave is subsequently vented and the solvent evaporated off. The residue is treated with ethyl ether and the solution is filtered. There are obtained 0.35 grams of an insoluble residue which is composed by an admixture of selenium, which is thus recovered, and N,N'-diphenylurea. The ethereal solution is evaporated to dryness and the residue is crystallized from benzene-petroleum ether. There are thus obtained 1.4 grams of a product which melts at 120° C and exhibits a characteristic IR absorption in the 6-micron area. The elemental analysis has given the following results:

C = 68.5%; H = 5.2%; S = 14.0%; N = 6.5%; For $C_{13}H_{11}NOS$ there should be: C = 68.1%; H = 4.8%; N = 6.1%; S = 13.9%; Yield 61%.

The compound as obtained in the present Example and in the preceding ones have been identified and analyzed by comparison with the homolog compounds as obtained with conventional syntheses.

EXAMPLE 13

A 180-mls autoclave is charged with 1.24 grams of 2.4-diaminotoluene (10 millimols), 1.88 grams of dimethyldisulphide, (20 millimols), 0.031 grams of selenium, 0.0360 grams of triethylamine and 20 mls of acetonitrile. The autoclave is filled with carbon monoxide at 4 atmospheres and the contents is left stirred at room temperature. During a period of 5 hours there are absorbed 10 millimols of carbon monoxide. By extending the reaction time at room temperature not any further gas absorption has been recorded. The autoclave is then heated to 60° C. At such a temperature the reaction mixture starts to consume carbon monoxide again and during 5-hour period there are absorbed 10 additional millimols of CO. The autoclave is opened and the as-formed solid is separated by filtration. There are thus obtained 2.04 grams of a product which melts at 185° C and which has given, at the elemental analysis, the following composition:

C = 49.5%; H = 5.4%; N = 10.6%; S = 24.0%; For $C_{11}H_{14}S_2N_2O_2$ there should be: C = 48.9%; H = 5.2%; N = 10.3%; S = 23.7%.

The compound thus obtained has been characterized by comparison with an original sample of toluene-2:4-dithiocarbamic acid-S:S'-dimethyl ester.

Yield 75%.

EXAMPLE 14

A 180-mls autoclave is charged with 1.24 grams of 2:4-diaminotoluene (10.2 millimols), 3.65 grams of diisobutylsulphide (20.4 millimols), 0.030 grams of selenium, 0.360 grams of triethylamine and 20 mls of acetonitrile. The autoclave is filled with carbon monoxide at 4 atmospheres and kept stirred at room temperature. During 6 hours there are consumed 10 millimols of carbon monoxide, 10 additional millimols of CO are absorbed during 6 hours of heating of the autoclave to 60° C. The autoclave is opened and the solvent removed in a vacuo. The residue is dissolved in benzene and the solution is filtered. The solid is composed by selenium which is thus recovered: from the solution, by addition of petroleum ether there are obtained 2.7 grams of a product which melts at 142° C and has the following composition:

C = 58.0%; H = 7.6%; N = 8.3%; S = 17.8%; For $C_{17}H_{26}S_2N_2O_2$ there should be: C = 57.6%; H = 7.4%; N = 7.9%; S = 18.1%.

The compound has been characterized by comparison with an original sample of toluene-2:4-dithiocarbamic acid-S,S'-diisobutylester.

Yield 75%.

EXAMPLE 15

A 180-mls autoclave is charged with 1.1 grams of p-phenylenediamine (10 millimols), 3 grams of diisobutyldisulphide (20 millimols), 0.030 grams of selenium, 0.360 grams of triethylamine and 20 mls of acetonitrile. The autoclave is charged with carbon monoxide at 4 atmospheres and kept stirred at room temperature. During 5 hours there are consumed 10 millimols of carbon monoxide. The temperature is then brought to 60° C and 3 hours are allowed to lapse. During this period, 6.5 additional millimols of CO are consumed. Without waiting the completion of the reaction, the autoclave is vented and the as-formed solid isolated by filtration. There are thus obtained 2.7 grams of a product which exhibits a characteristic IR absorption in the 6-micron area. The consumption of carbon monoxide and the quantity of isolated product are an evidence that a mixture of two products is involved, in which the phenylenediamine has been thiocarbonylated on a single aminic group and on both aminic groups, respectively. The NMR analysis of a this obtained sample permits to establish that the two products iso-$C_4H_9SCONH.C_6H_4.NH_2$ and (iso-$C_4H_9SCONH)_2.C_6H_4$ have been formed in the molar ratio of 1:2.

EXAMPLE 16

A 150-mls autoclave is charged with 1.46 grams of nor.butylamine (20 millimols), 1.88 grams of dimethyldisulphide (20 millimols), 0.03 grams of selenium and 40 mls of acetonitrile. The autoclave is cooled to −15° C and charged with carbon monoxide at 4 atmospheres. The contents of the autoclave is maintained stirred while the temperature is gradually raised to −5° C. The temperature is maintained at −5° C during 12 hours. During this period of time there are consumed by the reaction 19 millimols of carbon monoxide. The autoclave is opened, the solvent evaporated and the residue dissolved in petroleum ether. The selenium is collected on a filter and thus recovered. On removing the solvent by evaporation, there are obtained by sublimation of the residue at 50° C and $10^{-1}$ Torr, 2.15 grams of a product which melts at 35° C. This is identified by comparison with an original sample of nor.-butylthiocarbamic acid-S-methylester.

Yield 73%.

EXAMPLE 17

A 150-mls autoclave is charged with 1.46 grams of nor.butylamine (20 millimols), 4.9 grams of dibenzylsulphide (20 millimols), 0.03 grams of selenium and 40 mls acetonitrile. The autoclave is cooled to −5° C and charged with carbon monoxide at 4 atmospheres. The contents of the autoclave is maintained stirred at this temperature during 5 hours. The temperature is then allowed to rise to 10° C and stirring is continued during more than 4 hours. The reaction consumes 18 millimols of carbon monoxide. The solvent is stripped in a vacuo. The residue is dissolved in petroleum ether the selenium being thus collected on a filter and recovered. On cooling, there are isolated 3.8 grams of a product which melts at 60° C. It is identified by comparison with an original sample of nor.butylthiocarbamic acid-S-benzylester.

Yield 85%.

EXAMPLE 18

A 150-mls autoclave is charged with 1.2 grams of isopropylamine (20 millimols), 1.88 grams of dimethyldisulphide (20 millimols), 0.03 grams of selenium and 40 mls of acetonitrile. The autoclave is cooled to −15° C and charged with carbon monoxide at 4 atmospheres. The contents of the autoclave is kept stirred while the temperature is gradually increased to −5° C. The temperature is maintained at −5° during 12 hours. During this period there are consumed 19 millimols of carbon monoxide. The autoclave is opened, the solvent evaporated off and the residue dissolved in petroleum ether. By filtration and cooling of the solution there are isolated 2.05 grams of a product which melts at 71° C. It is identified by comparison with an original sample of isopropylthiocarbamic acid-S-methyl ester.

Yield 77%.

EXAMPLE 19

A 150-mls autoclave is charged with 0.60 grams of isopropylamine (10 millimols), 2.2 grams of biphenyldisulphide (10 millimols), 0.03 grams of selenium and 80 mls of acetonitrile. The autoclave is cooled to −15° C and charged with carbon monoxide at 4 atmospheres. The contents of the autoclave is kept stirred at this temperature during 1.5 hours. During this period there are consumed 10 millimols of carbon monoxide. The autoclave is opened, the solvent evaporated off and the residue dissolved in ethyl ether. The selenium is filtered off. By addition of petroleum ether to the solution and cooling there are isolated 1.6 grams of a product which melts at 100° C. It is identified by comparison with an original sample of isopropylthiocarbamic acid-S-phenyl ester.

Yield 82%.

EXAMPLE 20

A 150-mls autoclave is charged with 0.73 grams of tert.butylamine (10 millimols), 2.2 grams of biphenyldisulphide (10 millimols), 0.03 grams of selenium and 80 mls of acetonitrile. The autoclave is cooled to −15° C and charged with carbon monoxide at 4 atmospheres. The contents of the autoclave is maintained stirred at this temperature during 3 hours. During this period of time there are consumed 9 millimols of carbon monoxide. The autoclave is opened, the solvent evaporated off and the residue dissolved in ethyl ether. Selenium is filtered off and by adding petroleum ether to the solution there are isolated 1.67 grams of a product which melts at 110° C. It is identified by comparison with an original sample of tert.-butylthiocarbamic acid-S-phenylester.

Yield 80%.

EXAMPLE 21

A 150-mls autoclave is charged with 0.99 grams of cyclohexylamine (10 millimols), 2.2 grams of biphenyldisulphide (10 millimols), 0.030 grams of selenium and 80 mls of acetonitrile. The autoclave is cooled to −15° C and charged with carbon monoxide at 4 atmospheres. The contents of the autoclave is kept stirred at this temperature during 2 hours. During such a period of time, 9 millimols of carbon monoxide are consumed. The autoclave is opened, the solvent evaporated off and the residue dissolved in ethyl ether. The selenium is filtered off and by addition of petroleum ether there are isolated 2.0 grams of a product which melts at 111° C.

It is characterized by comparison with an original sample of cyclohexylthiocarbamic acid-S-phenyl ester.

Yield 81%.

EXAMPLE 22

A 150-mls autoclave is charged with 0.58 grams of 1:6-diaminohexane (5 millimols), 2.2 grams of biphenyldisulphide (10 millimols), 0.03 grams of selenium and 40 mls of acetonitrile. The autoclave is cooled to −10° C and charged with carbon monoxide at 4 atmospheres. This temperature is maintained and the contents of the autoclave is stirred during one hour. The temperature is allowed slowly to rise to +10° C and the latter temperature is maintained during three hours. 9.8 millimols of carbon monoxide are thus consumed as a total. The autoclave is opened and the resultant suspension is slurried with 40 additional mls of acetonitrile while heating to 80° C in order to dissolve the reaction product. Selenium is filtered off in hot conditions and is thus recovered. From the solution, 1.8 grams of a product which melts at 135° C are crystallized by cooling. The product has been identified by comparison with an original sample of hexane-1:6-dithiocarbamic acid-S,S'-biphenylester.

Yield 93%.

EXAMPLE 23

A 150-mls autoclave is charged with 15 millimols of $NH_3$ and 10 millimols of $CH_3SSCH_3$ dissolved in 20 mls of ethanol. There are added 0.030 grams of selenium and carbon monoxide is compressed to 4 atmospheres while maintaining the temperature of the autoclave at 25° C. During two hours the reaction consumes 9 millimols of CO. The autoclave is discharged and the solution is evaporated to dryness. The residue is taken up with ethyl ether and the undissolved selenium is filtered off. By evaporation of the solution, there are obtained 0.75 grams of a product which melts at 104°–105° C. It is identified by the elemental analysis and by comparison with an original sample of thiocarbamic acid-S-methylester.

Yield relative to the disulphide: 82%.

EXAMPLE 24

A 150-mls autoclave is charged with 15 millimols of $NH_3$ and 11.7 millimols of $C_6H_5-S-S-C_6H_5$ dissolved in 20 mls of ethanol. There are added 0.030 grams of Se and carbon monoxide is compressed to 4 atmospheres while maintaining the temperature of the autoclave at 25° C. In two hours the reaction consumes 8.5 millimols of CO. The autoclave is discharged and the solution is evaporated to dryness. The residue is taken up with ethyl ether, filtered and by adding to the solution petroleum ether there are isolated 1.4 grams of a product which melts at 91°–93° C. It is identified by elemental analysis and also by comparison with an original sample of thiocarbamic acid-S-phenylester.

The yield is 78% relative to the disulphide.

EXAMPLE 25

A 210-mls autoclave is charged with 20 millimols of iso-$C_3H_7NH_2$, 18.5 millimols of $(HOCH_2CH_2S)_2$, 0.05 grams of Se and 40 mls ethanol. Carbon monoxide is compressed to 4 atmospheres while maintaining the autoclave temperature at 25° C. In three hours there are absorbed 18 millimols of CO. The autoclave is discharged and the solution evaporated to dryness. The residue is dissolved in ethyl ether and selenium is filtered off. By evaporation of the solvent there are obtained 2.9 grams of a product which melts at 40° C. It is identified by the elemental analysis and IR analysis as N-isopropylthiocarbamic acid-S-(2-hydroxyethyl) ester.

Yield 96%.

EXAMPLE 26

A 210-mls autoclave is charged with 20 millimols of cyclohexylamine, 21 millimols of $(HOCH_2CH_2S)_2$, 0.050 grams of Se and 20 mls of ethanol. Carbon monoxide is compressed to 4 atmospheres and the autoclave temperature is maintained at 25° C. In 3 hours the reaction consumes 20 millimols of CO. The autoclave is discharged and the solution is evaporated to dryness. The solid is taken up with ethyl ether and selenium is filtered off. By evaporation of the solvent there are obtained 4 grams of a product which melts at 35° C. It is identified by the elemental and IR analyses as N-cyclohexyl-thiocarbamic acid-S-(2-hydroxyethyl) ester.

Yield 94%.

EXAMPLE 27

A 200-mls autoclave is charged with 2.0 grams of 4:4'-diaminodiphenylmethane (10.2 millimols), 20.4 millimols of $(CH_3S)_2$, 0.035 grams of Se and 0.150 grams of diazobicyclooctane dissolved in 40 mls of acetonitrile. The autoclave is charged with carbon monoxide at 4 atmospheres and kept stirred at 50° C. After 4 hours there have been consumed 8.5 millimols of CO. The solution is filtered and the filtrate is washed with acetonitrile. The thusly isolated solid (2.6 grams) melts at 180°–181° C. It has been identified by elemental analysis and by comparison with an original sample of diphenylmethane-4:4'-bis(thiocarbamic acid)-S:S'-dimethylester.

Yield 76%.

What we claim is:

1. A method for the preparation of esters of thiocarbamic acids comprising the step of reacting carbon monoxide and organic disulphides having the formula R'—S—S—R wherein R and R', equal to or different from each other, represent hydrocarbon radicals, either unsubstituted or substituted, with compounds having the formula:

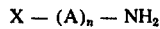

$$X - (A)_n - NH_2$$

wherein A is an arylene radical, either unsubstituted or substituted with halogens, hydrocarbon radicals, alkoxy groups, or it can be an alkylene radical having from 1 to 15 carbon atoms, either straight or branched, unsubstituted or substituted, in which n can be 0 or 1, whereas X can be hydrogen, —$NH_2$, or it can be the group $H_2N—Z—$, in which the bivalent function Z derives from alkyl, aryl, cycloalkyl, alkaryl, aralkyl radicals, in their turn unsubstituted or substituted.

2. A method according to claim 1, characterized in that the reaction takes place in the presence of a catalyst system composed by elemental selenium.

3. A method according to claim 2 characterized in that, in the case that A is an arylene radical, the catalyst system, in addition to elemental selenium, is also composed by a tertiary amine.

4. A method according to claim 1, characterized in that the pressure ranges from 1 to 200 atmospheres.

5. A method according to claim 1, characterized in that the temperature ranges from −20° C to 150° C.

6. A method according to claim 5, characterized in that, in the case that A is an alkylene radical, the temperature ranges from −20° C to 25° C.

7. A method according to claim 2 wherein R' and R are methyl; X is hydrogen, A is phenylene and $n$ is 1.

8. A method according to claim 2 wherein R' and R are methyl X is hydrogen; A is methylphenylene and $n$ is 0.

9. A method according to claim 2 wherein R' and R are methyl X is hydrogen; A is p-chlorophenylene and $n$ is 0.

10. A method according to claim 2 wherein R' and R are isobutyl; X is hydrogen, A is phenylene and $n$ is 1.

* * * * *